US007910353B2

(12) United States Patent
Shaffer et al.

(10) Patent No.: US 7,910,353 B2
(45) Date of Patent: Mar. 22, 2011

(54) METHODS AND APPARATUSES FOR ACHIEVING PRECISION GENETIC DIAGNOSES

(75) Inventors: Lisa G. Shaffer, Colbert, WA (US); Bassem A. Bejjani, Colbert, WA (US)

(73) Assignee: Signature Genomic Laboratories, Spokane, WA (US)

( * ) Notice: Subject to any disclaimer, the term of this patent is extended or adjusted under 35 U.S.C. 154(b) by 199 days.

(21) Appl. No.: 11/057,088

(22) Filed: Feb. 11, 2005

(65) Prior Publication Data

US 2005/0181410 A1 Aug. 18, 2005

Related U.S. Application Data

(60) Provisional application No. 60/544,877, filed on Feb. 13, 2004, provisional application No. 60/576,890, filed on Jun. 3, 2004.

(51) Int. Cl.
*C12Q 1/68* (2006.01)
*C12Q 1/70* (2006.01)
*C12M 1/34* (2006.01)
*G01N 33/48* (2006.01)

(52) U.S. Cl. ............... 435/287.2; 435/5; 435/6; 702/19; 702/20

(58) Field of Classification Search ............... None
See application file for complete search history.

(56) References Cited

OTHER PUBLICATIONS

Bejjani et al., "Use of Targeted Array-Based CGH for the Clinical Diagnosis of Chromosomal Imbalance: Is Less More?", American Journal of Medical Genetics, 2005, pp. 259-267, volume-issue 134A, Wiley-Liss, Inc., U.S.
Qian et al., "Identification and correction of spurious spatial correlations in microarray data," *BioTechniques* 35(1):42-48, 2003.
Misra et al., "A complex rearrangement of chromosome 7 in human astrocytoma," *Cancer Genetics and Cytogenetics* 151:162-170, 2004.

*Primary Examiner* — Shubo (Joe) Zhou
(74) *Attorney, Agent, or Firm* — Seed IP Law Group PLLC

(57) ABSTRACT

Methods and apparatuses for selecting and arranging clinically relevant chromosomal loci allow an exemplary diagnostic array to simultaneously test for numerous genetic alterations that occur in many different parts of the human genome. Clinically irrelevant or ineffective loci are eliminated. One implementation increases reliability and accuracy by dividing the base-pair sequence of each chromosomal locus into segments and then assigning nucleic acid clones for comparative genomic hybridization to each different segment. The segments may overlap for increased resolution and control. Clones representing segments that are adjacent on a native chromosome are placed in non-adjacent target areas of the array to avoid interfering hybridization reactions. Arrangement motifs within an array may be redundantly repeated for high availability and increased reliability and accuracy of results. Techniques, hardware, software, logic engines, loci collections, and diagnostic arrays are described.

9 Claims, 12 Drawing Sheets

METHODS AND APPARATUSES FOR ACHIEVING PRECISION GENETIC DIAGNOSES

RELATED APPLICATIONS

This application claims priority under 35 U.S.C. §119(e) to U.S. Provisional Applications, Nos. 60/544,877 to Shaffer and Bejjani, filed Feb. 13, 2004 and 60/576,890 to Shaffer and Bejjani, filed Jun. 3, 2004.

TECHNICAL FIELD

The subject matter relates generally to molecular biology and more specifically to methods and apparatuses for achieving precision genetic diagnoses.

BACKGROUND

Chromosome analysis is an important component in diagnosing congenital anomalies that cause physical and mental developmental delay. Cytogenetic imbalance results in DNA copy-number changes and alteration in gene dosage in the altered chromosomal segment(s). These changes may result in abnormal clinical phenotypes. Such chromosomal aberrations are conventionally detected by a variety of methods, each with distinct advantages and disadvantages. Routine cytogenetic analysis by GTG banding can achieve a resolution sufficient to detect aneuploidy and structural rearrangements of base-pair sequences greater than five megabases (Mb) but cannot reliably identify abnormalities less than five Mb.

More subtle genetic alterations or those involving regions that are difficult to visualize may be undetectable by conventional cytogenetic techniques (e.g., these include most microdeletion syndromes and exchanges of similarly banded segments that lead to cryptic translocations). Fluorescence in situ hybridization (FISH) was developed to probe individual chromosomal loci at a resolution equal to the size of the probe (e.g., 35-200 kilobases (Kb)). Only a few loci may be examined at a time, however, and FISH can usually only be performed in a limited manner based on phenotype. Thus, single locus FISH is not an appropriate screening tool for the analysis of more than a few loci at a time.

Additional molecular cytogenetic techniques were developed to overcome these limitations. Comparative genomic hybridization (CGH) was developed to identify chromosomal imbalance without the need for phenotypic information, circumventing multiple FISH experiments. CGH provides genome-wide screening of genetic sequence alterations by comparing differentially labeled test and control samples of genomic DNA. The resolution of the technique, however, is still limited to approximately 5-10 Mb because metaphase chromosomes are used as the targets for analysis.

To substantially increase the resolution, CGH-based microarrays for performing "array CGH" were developed. Array CGH is a high-resolution, comprehensive method for detecting both genome-wide and chromosome-specific copy-number imbalances. Array CGH typically uses large-insert clones (such as bacterial artificial chromosomes, "BACs") as the target for analysis rather than metaphase chromosomes. As a consequence, the resolution of the array is limited only by the size of the insert used and the physical distance in the human genome between clones that are selected for the array.

CGH microarrays have been successfully constructed to test many parts of the human genome. In 2001, a whole-genome array was constructed using approximately 2400 BAC clones to scan for genome-wide copy-number alterations. An array covering some of the telomeric regions of the human genome has also been developed. Individual chromosomal regions have also provided good targets for array CGH. For example, in 2003 a microarray was designed to cover much of the most distal 10.5 Mb of chromosome location 1p36 to study subjects with monosomy 1p36. In 2003, an array was constructed based on chromosome 18 to study patients with congenital anal atresia. Microarrays have also been developed to test parts of chromosomes 20 and 22.

As shown in FIG. 1, conventional CGH microarrays 100 constructed for research purposes are designed to screen chromosomal regions or the entire genome for chromosomal segment gains or segment losses with improved resolution over earlier techniques. For many reasons, however, most of these are not appropriate or relevant for use in clinical genetic diagnosis. First, most conventional BACs used in these microarrays have been culled from BAC databases without prior external verification of the exact locations ("loci") that they map to ("cover") on a chromosome 102. Second, these databases rarely provide notice that some of the BACs map to multiple loci, even on entirely different chromosomes 104. Third, many of the loci that are covered by a single clone may show dosage variation due to the inherent technical variability of the procedures involved 106. Fourth, the conventional CGH microarray 100 may identify alterations in regions of the genome that do not have established clinical relevance 108. Thus, such conventional "whole genome" arrays are likely to generate data that are difficult to interpret or that are inaccurate in that they present multiple false positive results 110. That is, alterations in regions of the genome that do not have established clinical relevance are impossible or, at the very least, expensive to interpret and/or verify in a clinical setting 112.

In a clinical setting, a conventional whole-genome approach to array CGH may cause erroneous test results that result from undesirable polymorphisms, which are usually abundantly represented in this approach. Data from sub-telomere FISH analysis, for example, reveal many telomeric alterations that possess no clinical significance.

It is estimated that about 35% of clones that are currently available from the public and private databases either map to the wrong location, map to more than one location in the genome, represent polymorphic areas of the genome, or contain repetitive sequences that may interfere with hybridization. Using random clones from the databases would result in a clinical test that has more than a 35% probability of error and that is of dubious utility. Thus, "whole genome arrays" arrays are not appropriate for clinical applications. The adoption of such "whole genome" arrays for use in clinical diagnostics may be unwise, not only leading to many false positive diagnoses that necessitate expensive follow-up confirmatory tests by FISH or other methods (e.g., 112); but also additional blood draws from unaffected relatives of the patient to determine possible segregation of genetic deletions, duplications, or polymorphisms; not to mention unnecessary anxiety for the family of a person being tested. In the "whole genome" approach, hybridization results for single clones that show dosage difference require careful examination and each clinical case may require all the time and expense of a mini-research project. Thus, genome-wide "dense" arrays that are conventionally available for research use are not appropriate, relevant, or efficient in a clinical setting. There exists a need for a clinically useful diagnostic array that provides reliability, that accurately detects chromosome abnormalities assayed, and that provides interpretable results with an acceptable degree of precision. Further, there exists a need for methods of precision genetic diagnosis that provide clinical confidence by interrogating clinically relevant parts of the genome rather than the clinically irrelevant parts.

SUMMARY

The subject matter described herein can be used in various fields to greatly improve the accuracy and reliability of nucleic acid analyses, chromosome mapping, and genetic testing of suspected genetic conditions. In one implementation, aspects of the subject matter are incorporated into the construction of a diagnostic array ("array"), such as a temporal array, or a spatial array of tests used, for example, in comparative genomic hybridization (CGH) microarrays. An exemplary high-availability diagnostic array for testing chromosomal loci associated with human disease and constructed according to aspects of the subject matter may use one or more exemplary features, including: selective screening of genetic loci, reliable coverage of the selected loci, strategic placement of control reference clones, strategic nonrandom distribution of the clones on the microarray, and/or redundant sub-arrays for comparison and dependability.

The subject matter allows error-resistant and high-availability testing of nucleic acid sequence alterations, such as genetic sequence and base-pair alterations, deletion or duplication of genetic sequence (each loosely referred to herein as "genetic alterations") that may represent anomalies associated with a disease. In the case of an exemplary CGH microarray implementation, clinically relevant chromosomal loci are carefully selected for their diagnostic efficacy, and the overall base-pair sequence of each chromosomal locus of interest is parsed or disassembled into multiple contiguous and/or overlapping segments. Each segment—as represented by a nucleic acid clone or synthesized oligonucleotide—is isolated into a reliable individual test area target on the microarray, free from the hybridization influences of adjacent sequences that occur on a native chromosome.

Clones representing each individual segment may be included many times and in different positions in different sub-arrays of an exemplary array. When a test is complete, redundant occurrences of an individual segment test are compared with each other, and the test results of the segments are logically reassembled back into a combined test result for the overall base-pair sequence of the chromosomal locus of interest. Because the testing of each chromosomal locus is typically broken up into multiple segments for isolated and reliable testing; because the multiple segments are typically selected to overlap each other; and because each segment is tested redundantly; an exemplary diagnostic array achieves unprecedented diagnostic resolution, precision, and reliability.

Loci to be included in an exemplary array are screened from the outset for their diagnostic usefulness and efficacy, and only clones that uniquely and reliably map to these loci are allowed in an exemplary array, thus assuring clinically relevant and reliable test results. In other words, loci from "deadwood" parts of the genome are excluded from inclusion and in addition, dependable clones are substituted for undependable ones.

Although an exemplary array limits genetic testing to only chromosomal loci and related regions that provide clinically useful information, an exemplary microarray is comprehensive because chromosomal loci are drawn from clinically relevant regions across the entire human genome, including the telomeric and pericentromeric regions. In other words, in one implementation, an exemplary diagnostic array comprises a very comprehensive battery of diverse tests that usually have to be performed separately at great cost. Moreover, an exemplary microarray provides unprecedented accuracy and reliability for diagnosing myriad genetic alterations—in one single test.

DETAILED DESCRIPTION

Overview

The subject matter described herein can be used in various fields to greatly improve the accuracy and reliability of nucleic acid analyses, chromosome mapping, and genetic testing, e.g., for diagnosing genetic diseases and cancer. In an implementation that uses a diagnostic array (hereafter, "array"), such as a microarray used for comparative genomic hybridization (CGH), a comprehensive battery of clinically relevant chromosomal loci are carefully selected and screened to provide stringent diagnostic efficacy. Selected loci are included on an exemplary array. Significantly, clinically irrelevant chromosomal loci—vast portions of the human genome that are irrelevant for making diagnoses—are carefully eliminated from being candidates for positions on an exemplary array. These latter inefficacious parts of the genome not only have no utility for providing clinically useful information, but actually impede accurate and efficient diagnoses in many ways.

The overall genetic code sequence ("base-pair sequence") of each clinically relevant chromosomal locus selected for an array may be parsed or disassembled into multiple contiguous and/or overlapping segments. Each segment—as represented by a nucleic acid clone or synthesized oligonucleotide—is isolated into a reliable individual test area ("target") on an exemplary array, free from interfering influences (on hybridization) of clones that represent adjacent sequences that occur on a native chromosome.

A clone representing an individual segment of the base-pair sequence of a chromosomal locus may be included multiple times and in different positions within different sub-arrays of an exemplary array.

When a patient's chromosomal material is tested against the exemplary array, redundant occurrences of a given individual segment test are compared with each other, and test results of the multiple segments of a locus are collated, that is, logically reassembled back into a single combined test result for the overall base-pair sequence of the locus.

Figure 1:
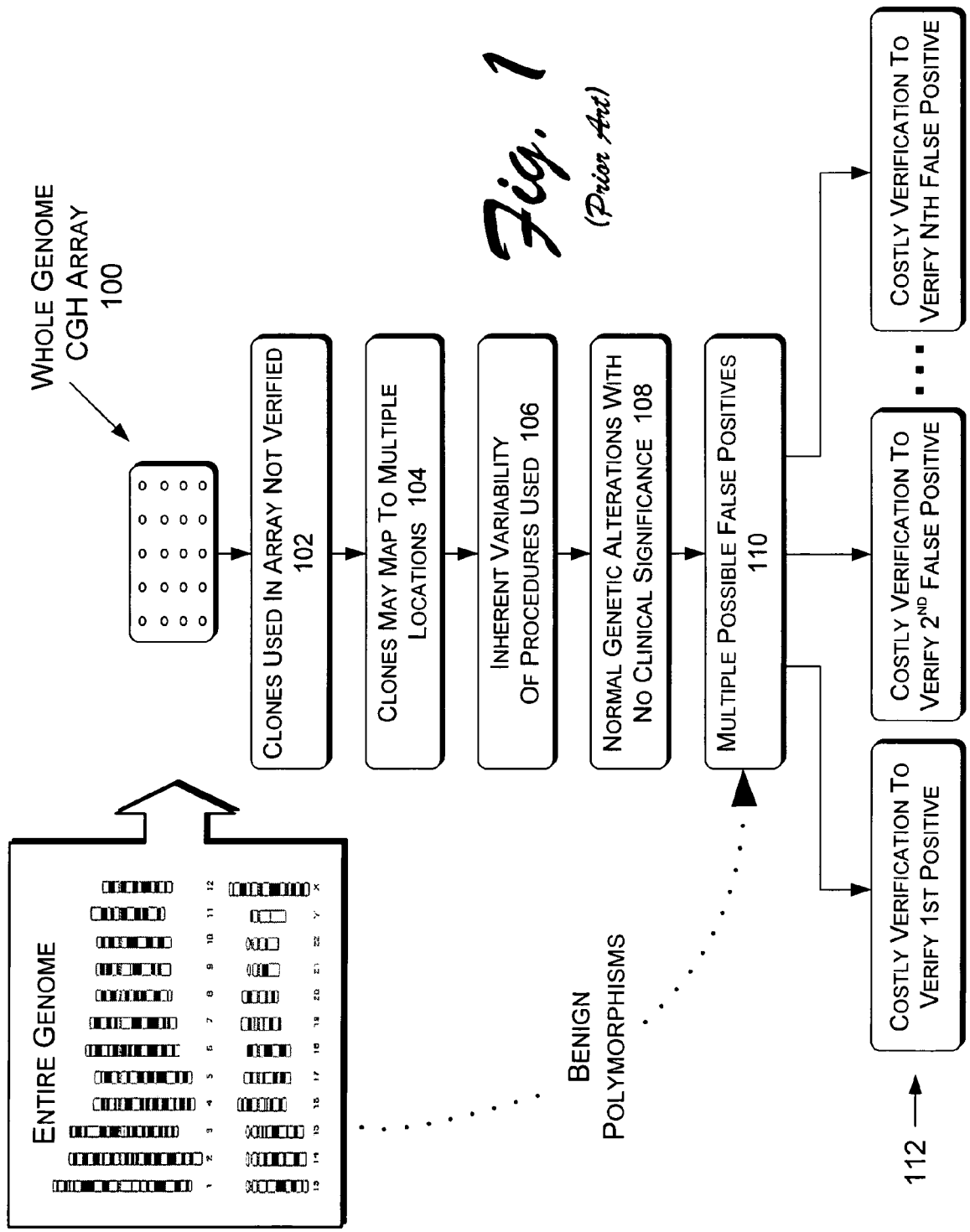
FIG. 1 is a flowchart describing problems encountered with "whole genome" comparative genomic hybridization arrays.
Figure 2:
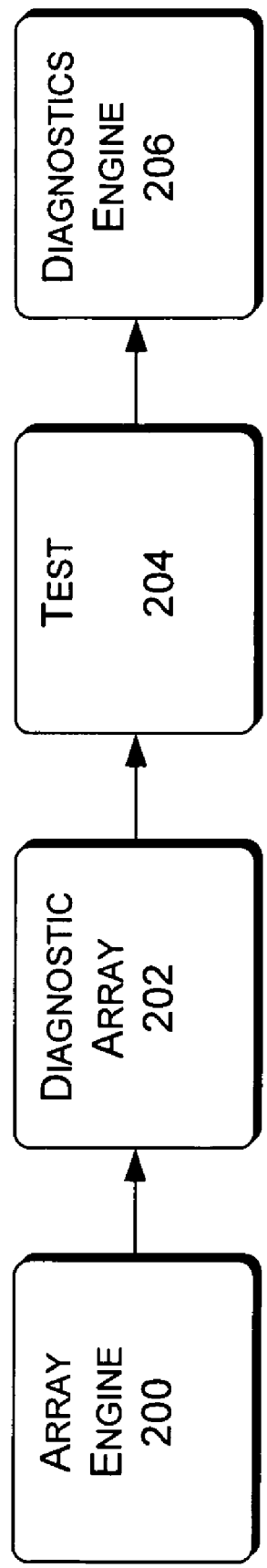
FIG. 2 is a block diagram of an exemplary system for achieving precision genetic diagnoses.

In one implementation shown in FIG. 2, aspects of the subject matter are incorporated by an array engine 200 into the construction of a high-availability array 202. An exemplary array 202 undergoes test conditions 204 using chromosomal loci selected to test for disease and the resulting clinically reliable information can be logically processed, for example, by an exemplary diagnostic engine 206 in order to support very precise diagnoses.

By simultaneously testing clinically relevant chromosomal loci strategically selected from across the entire human genome, including the telomeric and pericentromeric regions of chromosomes, an exemplary array 202 provides for convenience, cost savings, and diagnostic efficacy.

Figure 3:
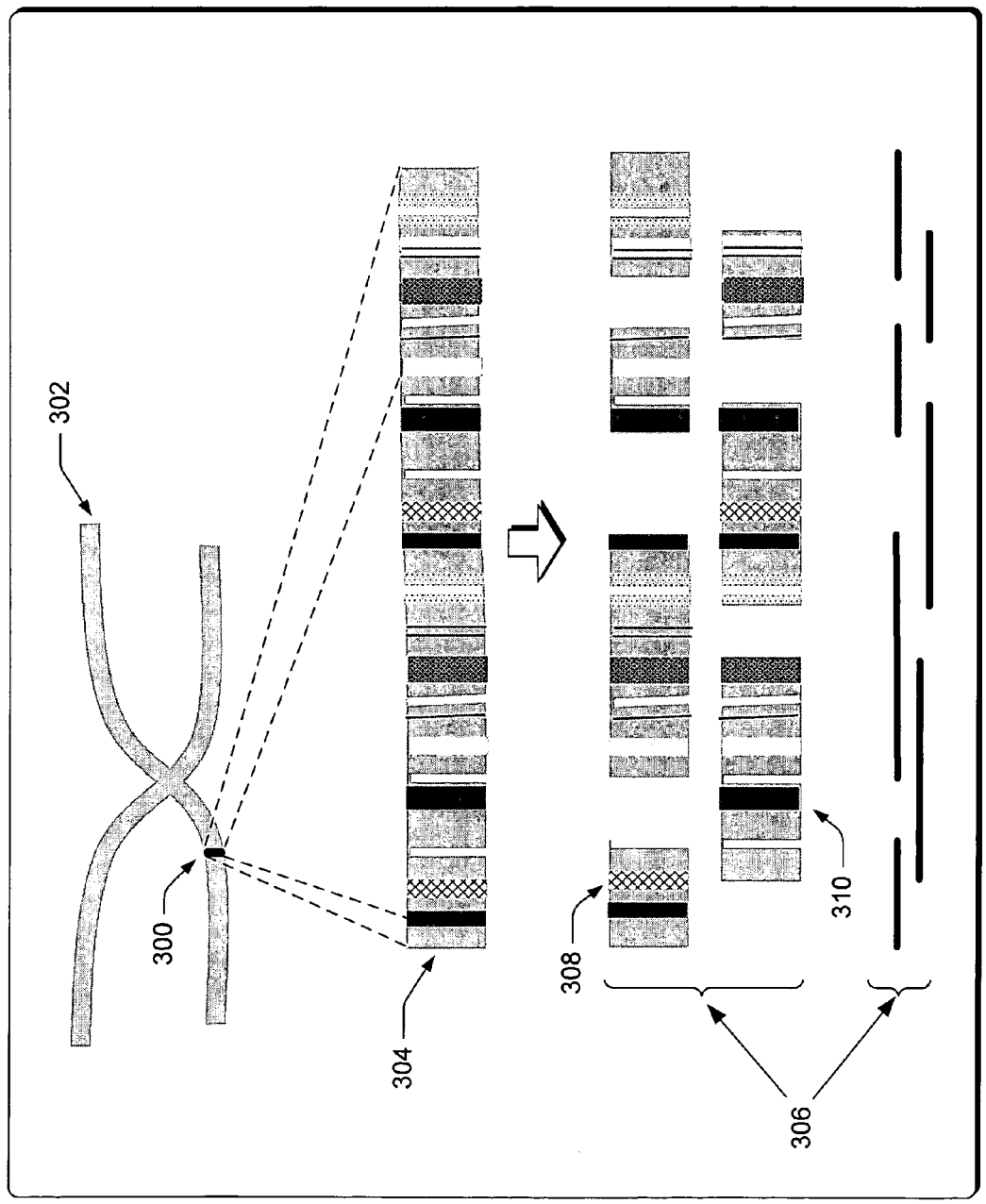
FIG. 3 is a graphic representation of an exemplary division of a clinically relevant chromosomal locus into overlapping segments.

FIG. 3 shows a chromosomal locus 300 that possesses a base-pair sequence 304 located on a chromosome 302. The base-pair sequence 304 of this locus 300 (and each locus) to be included for testing in or on an exemplary array 202 may be divided into two or more "layers" of segments 306, which are also illustrated as segment lines. Nucleic acid clones or alternatively, synthesized oligonucleotides, are assigned to represent the segments 306 of each locus 300. The clones now representing the base-pair sequence 304 of respective segments 306 are strategically positioned in individual targets of an exemplary array 202 in a manner that avoids interaction and interpretive errors between adjacent segments that neighbor each other (e.g., 308 and 310) on the native chromosome 302.

In one implementation, overlapping segments, such as those shown in FIG. 3, can also be used for increased test resolution and certainty of diagnosis. In response to a test 204, the test results for each overlapping segment of a chromosomal locus 300 are collated into a single combined test result for the overall base-pair sequence 304 of each locus 300, e.g., by an exemplary diagnostics engine 206.

Not only are the chromosomal loci carefully selected, but the aforementioned nucleic acid clones (or synthesized oligonucleotides) that are to represent the segments 306 comprising each locus 300 are carefully selected and screened (or synthesized) for faithful, accurate, and reliable mapping to their respective segments, as will be discussed more fully below.

Figure 4:
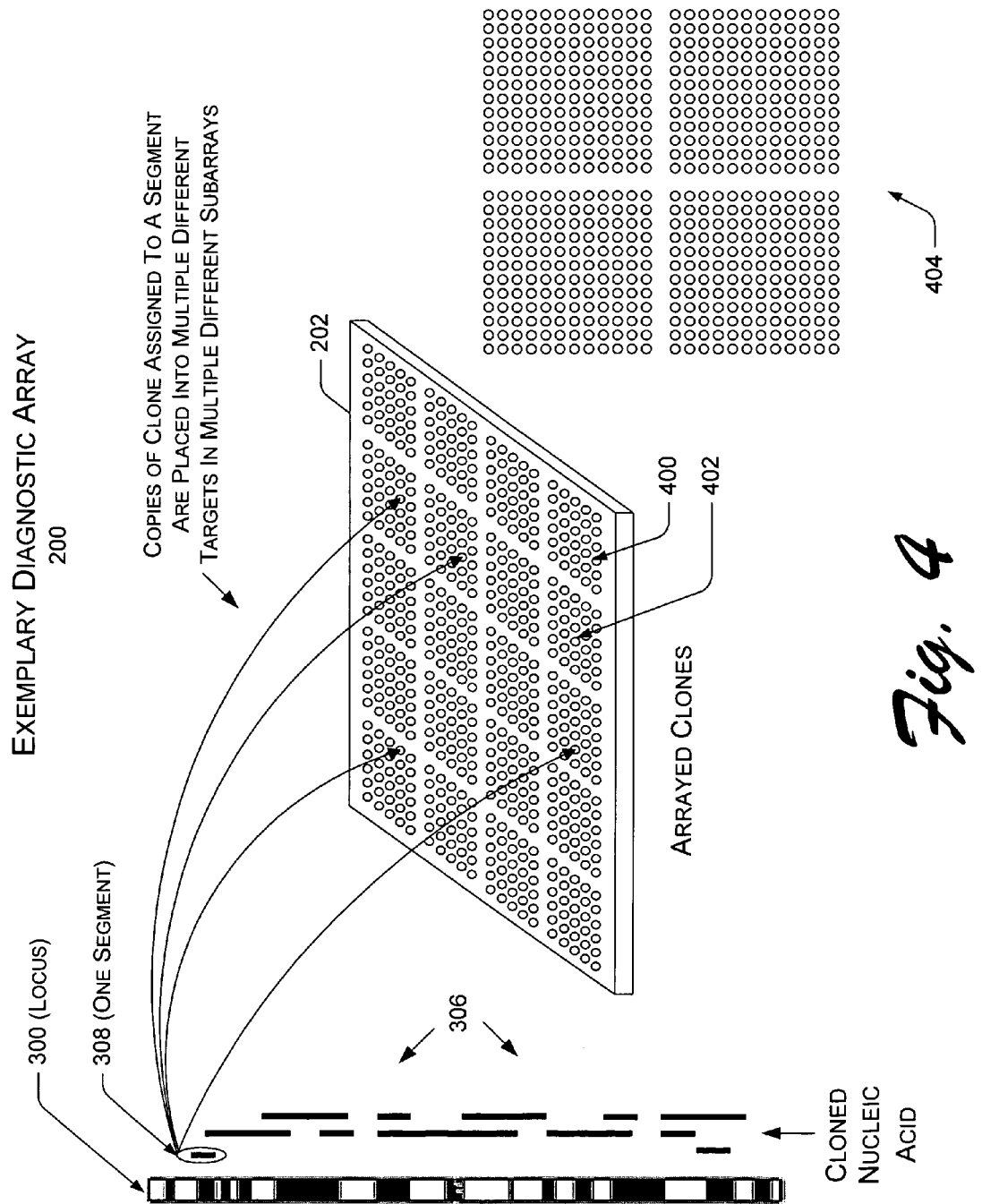
FIG. 4 is a graphic representation of an exemplary diagnostic array that uses segment isolation.

As shown in FIG. 4, in one implementation of an exemplary array 202, copies of clones assigned to a segment 308 of a chromosomal locus 300 may be placed into targets in multiple sub-arrays (e.g., 400, 402) to provide reliability and comparison. Moreover, groups of sub-arrays, such as an example four block sub-array 404, may be redundantly repeated in an exemplary array 202. On a larger scale, an exemplary array 202 consisting of redundantly repeated sub-arrays (e.g., 400, 402) may itself be redundantly repeated so that arrangement motif of the smallest sub-arrays are redundantly repeated on multiple larger scales. The amount of redundancy to be imparted to an array may be related to a diagnostic efficacy of part of the array, as discussed more fully below with respect to FIG. 11.

Control reference targets may be added to an array 202 for comparison with the individual target areas for testing a segment of a chromosomal diagnostic locus. Multiple clones flanking the chromosomal diagnostic locus ("flanking clones") may be selected and distributed on the array 202. In one implementation, the flanking clones are placed in a deliberate manner to separate them physically on the array if they are contiguous in the genome. These controls typically remain unaltered despite alteration in a diagnostic target of interest. Thus, the flanking controls provide a reliable reference for comparing the intensity of fluorescence signals across targets that are adjacent on the chromosome but far apart on an array 202.

Figure 5:
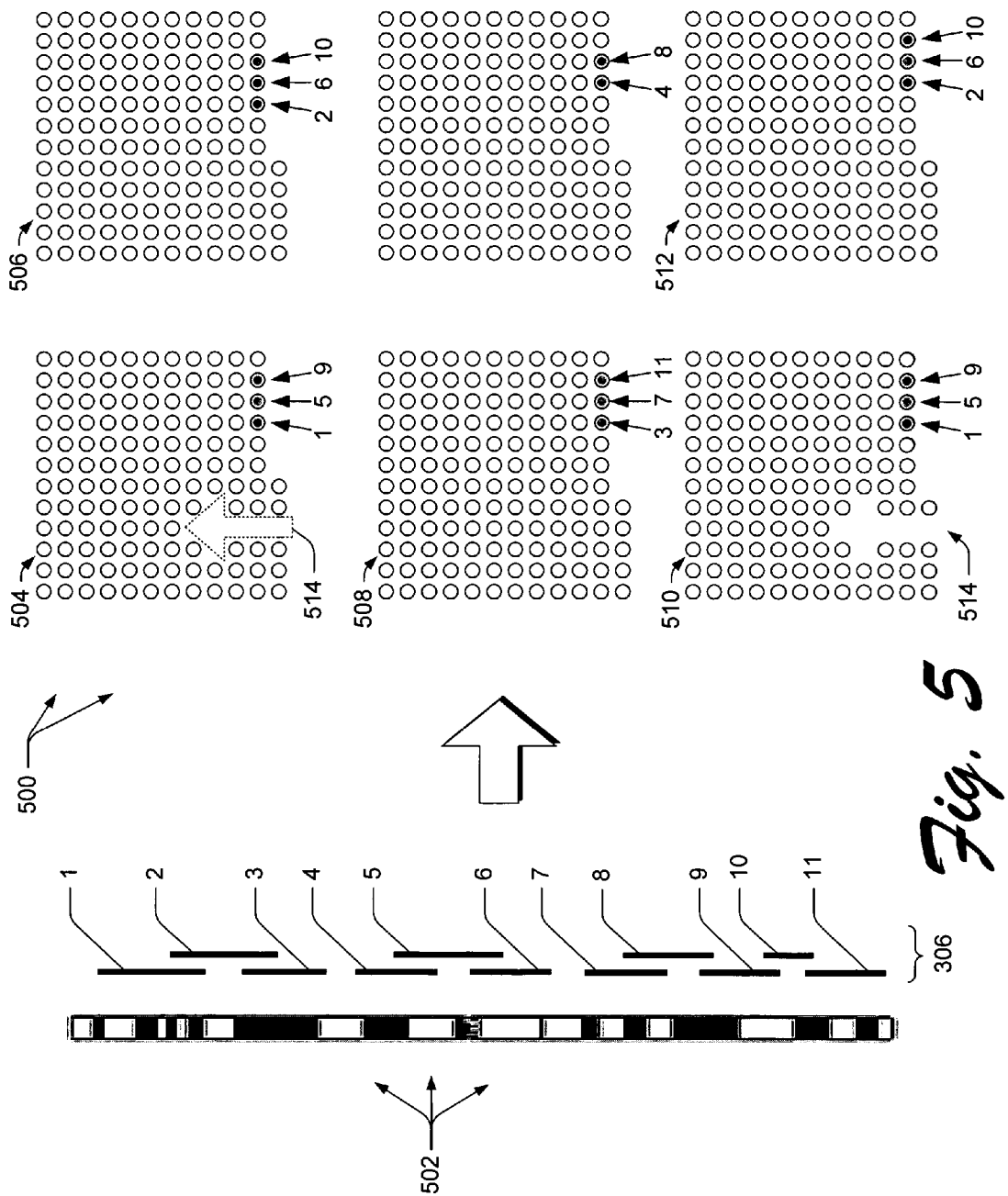
FIG. 5 is a graphic representation of an exemplary method for distributing segments of a clinically relevant chromosomal locus on an exemplary diagnostic array.

FIG. 5 shows an exemplary clone distribution 500, in which clones representing the segments 306 of one or more chromosomal loci 502 are strategically positioned in targets across an exemplary array 202 to avoid interaction between clones representing adjacent segments on the native chromosome 302.

In one implementation, a locus consisting of, for example, segments 1-3 (in FIG. 5) undergoes distribution of clones representing the segments in multiple sub-arrays of the exemplary array 202. For example, clones representing segment "1" are placed in sub-array 504, but not in the same sub-array as clones representing segment "2," which, because it is adjacent on the natural chromosome, is placed in sub-array 506 instead. Segment "3," which is adjacent to segment "2" on the natural chromosome, is represented by clones that are placed in sub-array 508 to avoid proximity to the clones for segment "2," etc. An exemplary clone distribution 500 may be redundantly repeated on several scale sizes, as discussed above. Thus, additional targets for clones representing segments "1," "5," and "9" may be repeated in sub-array 510, and additional targets for clones representing segments "2," "6," and "10" may be placed in sub-array 512, etc.

Thus, an exemplary array 202 implementation provides a comprehensive battery of diverse tests that can be performed relatively inexpensively compared to costly separate conventional tests. Moreover, such an exemplary array 202 provides unprecedented accuracy, reliability, and convenience for diagnosing a myriad of genetic alterations, for example, in one single CGH microarray test.

In one implementation, an arrangement motif for targets in sub-arrays may include an orientation feature for positioning an array 202 during testing. This orientation feature may be a marking or design that can be implemented by arranging the targets themselves, for example, by creating a non-symmetric arrangement of the targets on the array 202 to form an arrow, or other directional indicator 504. The directional indicator(s) 504 allow correct orientation of the array 202, e.g., during insertion of the array 202 into a diagnostics engine 206. These orientation markings or design let a machine and/or human operator recognize an array's orientation.

High Availability Aspect

High availability (HA) is a term used between artisans in various trades to refer to a system that is capable of providing reliable and/or accurate service almost all of the time. Provision of reliable HA genetic testing has been a longstanding problem. In one aspect of the subject matter, the exemplary methods described herein achieve HA genetic testing by creating very reliable components, by creating elements that are fault tolerant, by creating relationships between the elements that avoid error, and by creating subsystems that are backed up by redundant provisioning. In an exemplary array 202, "redundant provisioning" and "clustering" are design techniques that impart HA to genetic testing. Components within an exemplary array 202 or exemplary genetic testing system (FIG. 2) are replicated so that the testing functions of the system are carried out simultaneously in different parts, and if a subsystem—or a sub-array—fails, the test it performs is carried out by a "spare."

Thus, an exemplary array 202 constructed according to aspects of the subject matter provides many high-availability features. Nucleic acid sequences used on an exemplary array 202 are selected to provide quality information and diagnostic efficacy. Moreover, individual tests included on an exemplary array 202 are repeated redundantly for quality assurance and verification of test results. The placement of individual tests on an exemplary array 202 strategically eliminates many possibilities for hybridization errors and errors introduced by variations that occur within usual procedural tolerances.

Array Compression

Figure 6:
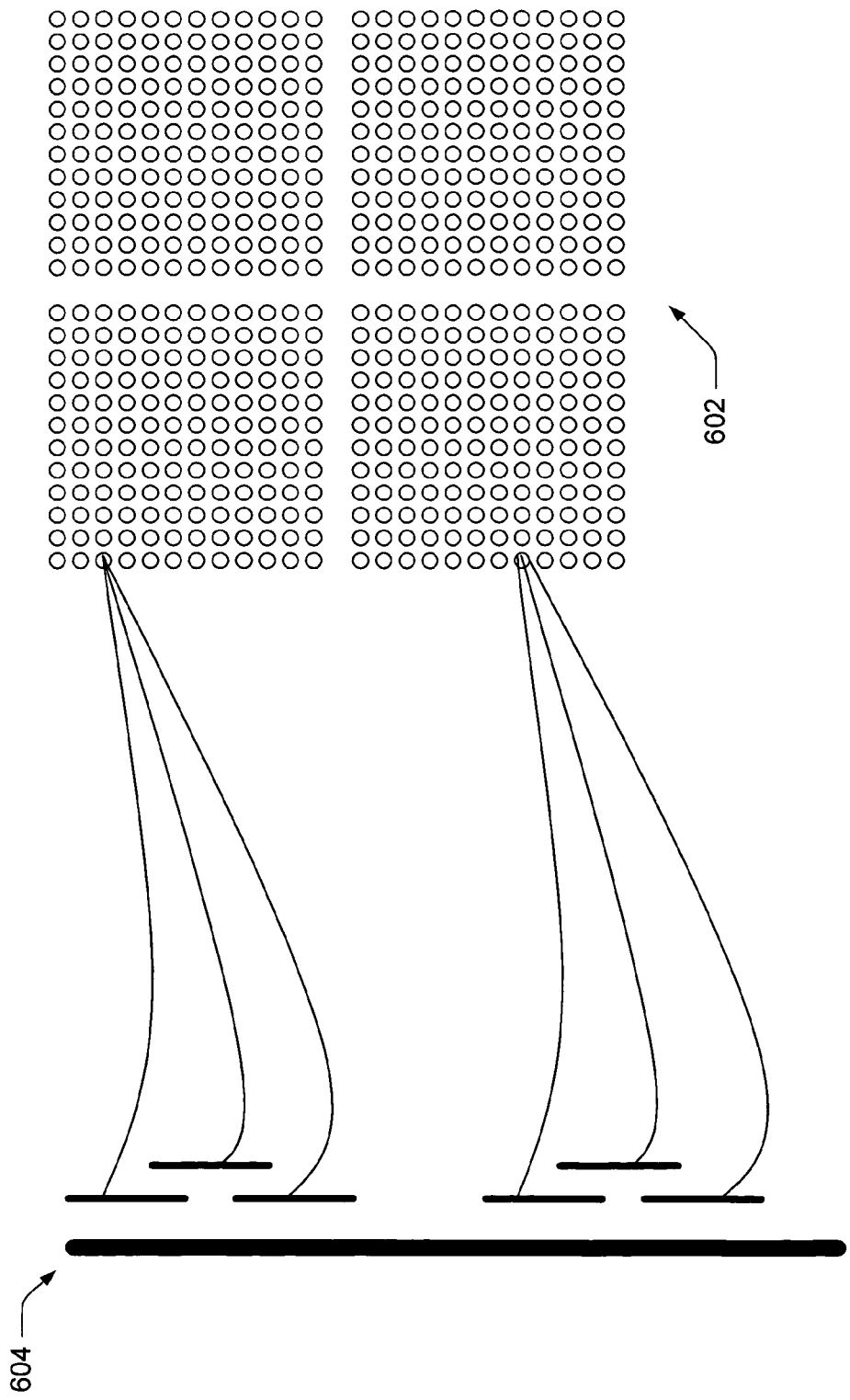
FIG. 6 is a graphic representation of an exemplary method for compressing an exemplary array by mixing targets for more than one chromosomal location.

FIG. 6 shows an exemplary method of producing a reduced size diagnostic array 602. In one implementation, when arraying DNA targets (BAC clones, cDNA, oligonucleotides, etc.) on an array 602, the DNA targets from more than one location on the genome 604 (2, 3, or more contiguous or noncontiguous locations on the genome) are mixed and the mixture spotted as a single target on the array 602. This technique simplifies the array 602 by reducing the number of targets that are arrayed on the array's solid support. For example, if an array contains 3,000 targets each representing a single BAC, the DNA from 3 contiguous (or noncontiguous) BACs can be pooled into a single tube, mixed, and spotted as a single target that contains a mixture of the 3 BACs. If this technique is performed for every 3 BACs, then the same genetic contents (that are present on the aforementioned 3,000-target array) can be present in an array 602 that has only 1,000 targets.

Exemplary Array Engine 200

Figure 7:
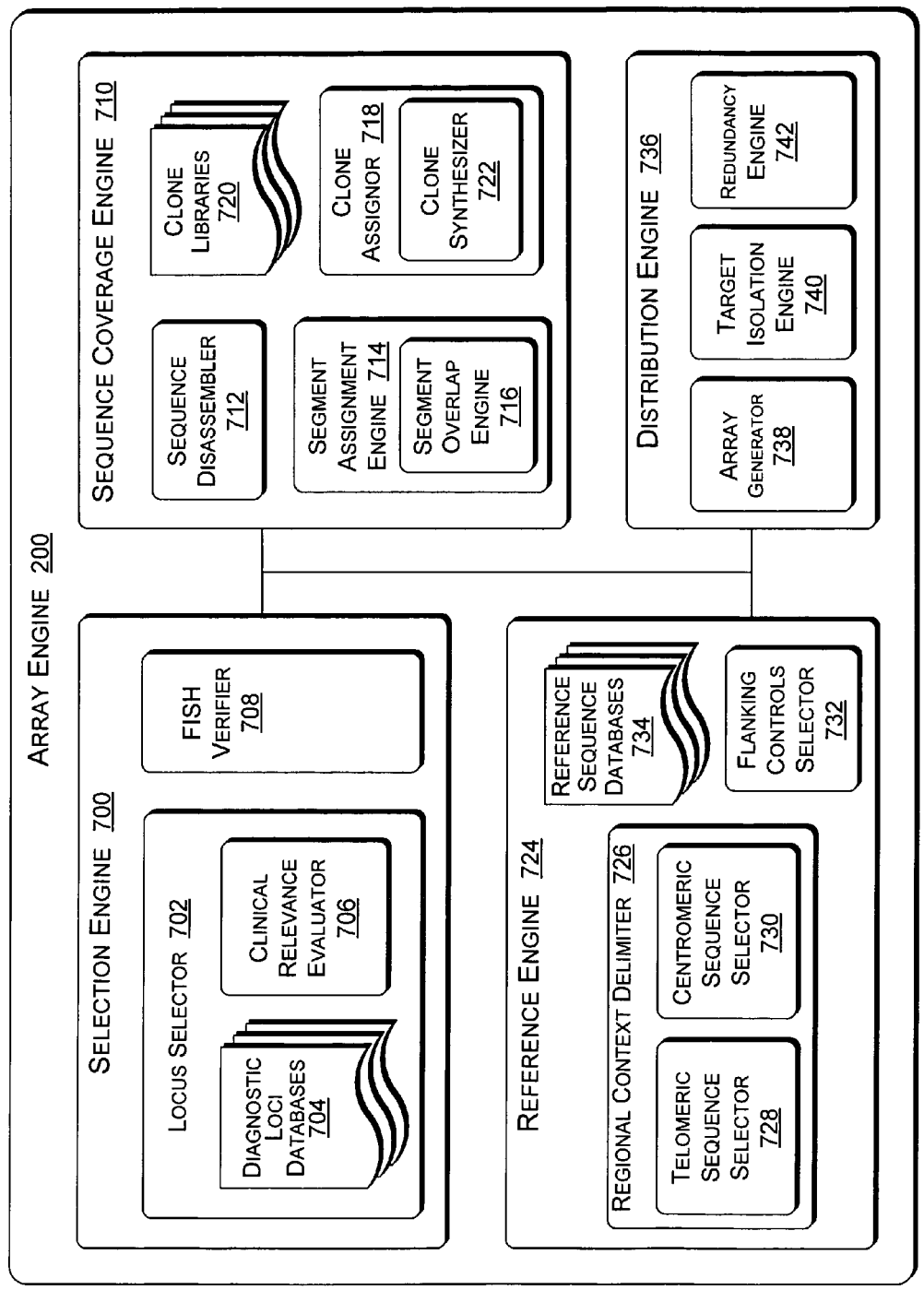
FIG. 7 is a block diagram of an exemplary array engine.

FIG. 7 shows an exemplary implementation of an array engine 200, in which various components are communicatively coupled to design, implement, and/or construct an exemplary array 202. The components of an exemplary array engine 200 are logic modules or, may be combinations of clinical processes, software, firmware, and/or hardware, and thus may include components or processes that can be performed manually in some implementations.

A selection engine 700 seeks to determine a set of chromosomal loci that have reliable diagnostic efficacy—that is, chromosomal loci capable of genetic alteration indicative of disease and reliably readable for indicating either a presence or an absence of the genetic alteration. A locus selector 702 included in the selection engine 700 may search or consult one or more diagnostic loci databases 704 from which a clinical relevance evaluator 706 decides which loci are to be included in the exemplary array 202. The diagnostic loci databases 704 may take into account population studies that help to determine the extent of deletion/duplication polymorphisms. For an exemplary array 202 that is to be used in a clinical application, diagnostic loci databases 704 that eliminate most latent polymorphisms allow the exemplary array 202 to avoid costly diagnostic procedures and counseling errors that result from misdiagnosing benign polymorphisms as disease-causing abnormalities.

A FISH verifier 708 coupled with the selection engine 700 may be used to confirm a base-pair sequence of a given locus, location of the sequence in the genome, or to test the diagnostic efficacy of a given locus prior to its inclusion in an exemplary array 202. More importantly, the FISH verifier 708 may also be used to reject clones from representing a certain segment of a locus. The rigorous assessment and screening of bacterial artificial chromosomes (BACs) and other nucleic acid targets and their use in an exemplary array is especially important when the array 202 is used for clinical diagnosis.

A sequence coverage engine 710 coupled with the selection engine 700 may assign multiple nucleic acid clones, each to represent a segment of a base-pair sequence of a chromosomal locus selected by the selection engine 700. The sequence coverage engine 710 may further include a sequence disassembler 712 to divide a base-pair sequence of a chromosomal locus into proposed segments according to a schema. For example the disassembler 712 may break apart a base-pair sequence into pieces that have a certain length, polarity, etc., that facilitates construction of the exemplary array 202 or the test procedures.

The sequence coverage engine 710 may include a segment assignment engine 714 to divide a base-pair sequence of a chromosomal locus or a chromosomal region associated with the locus into segments. The segment assignment engine 714 determines the segmentation strategy and logic for a given locus. Sometimes the segment logic is determined by availability of a clone or oligonucleotide to represent the desired segment. Thus, the segment assignment engine 714 may consult one or more clone libraries 720. In one implementation, the clone libraries 720 include large insert clones, capable of representing base-pair sequences, such as bacterial artificial chromosomes (BACs), yeast artificial chromosomes (YACs), P1-derived artificial chromosomes (PACs), cosmids, plasmids, cDNAs, etc., and/or synthetic oligonucleotides.

The segment assignment engine 714 may also include a segment overlap engine 716 to implement a base-pair sequence overlap strategy for the segments. Segment overlap can provide increased resolution and accuracy of test results, as overlapping portions of segments are, in a sense, tested twice, and because overlap results can be logically added or subtracted to the underlying segment logic of the base-pair sequence of a given chromosomal locus.

A clone assignor 718 may consult one or more clone libraries 720 to associate a clone with each segment of the base-pair sequence of a selected chromosomal locus. Alternatively, a clone assignor 718 may utilize services of a clone synthesizer 722 to create an oligomer of nucleic acid to represent a segment, for example, using PCR or other methods of nucleic acid synthesis and amplification.

A reference engine 724 may be communicatively coupled with the array engine 200 to incorporate additional base-pair sequences into targets of an exemplary array 202 to provide reference controls for comparison with hybridization results from targets for the chromosomal loci.

The reference engine 724 may also include a regional context delimiter 726 that further includes a telomeric sequence selector 728 and a peri-centromeric sequence selector 730 for selecting chromosomal regions in the vicinity of one of the chromosomal loci. Often, in the case of deletion or duplication syndromes, it provides useful information to test the context or nearby genetic environment of the locus of interest. These regions may be assigned clones and added to target areas of an exemplary array 202. If a genetic condition being diagnosed is a microdeletion syndrome, then the presence or absence of these regions in chromosomes of a patient being tested can be ascertained by the exemplary method to inform the diagnostician of the extent of a genetic deletion. Thus, genetic regions (centromeric and telomeric) adjacent to a locus of interest may also be included in an exemplary array 202, e.g., to test the extent of a microdeletion.

The reference engine 724 may also include a flanking controls selector 732. Clones that flank a clinically relevant locus can be selected and placed at random on an exemplary array 202 as reference clones—i.e., clones that are typically unaltered even in a patient that tests positive at the clinically relevant locus—thus providing a comparison and a further assurance of quality. The reference clones can provide a baseline signal strength for comparison with an adjacent or nearby clinically relevant locus when an exemplary array 202 is being evaluated. Hence, the flanking controls selector 732 may consult one or more reference sequence databases 734 to ascertain which additional base-pair sequences, if any, should be represented by clones and incorporated as flanking control targets to be logically associated with a chromosomal locus of interest, although not physically associated with the chromosomal locus of interest on the array 202.

A distribution engine 736 may be included in an exemplary array engine 200. An array generator 738 may be included in the distribution engine 736 to design the geometry and size of the exemplary array 202 with its various levels of sub-arrays. The geometry may depend on the number of genetic conditions being included for diagnosis; the number of segments used to represent each chromosomal locus associated with a genetic condition; and the amount of redundancy to be built into the exemplary array 202.

A target isolation engine 740 logically distributes clones representing segments that are adjacent on a native chromosome into non-adjacent targets on the exemplary array 202. In other words, the target isolation engine 740 provides the measure of spatial isolation for clones representing adjacent segments of a chromosomal locus.

A redundancy engine 742 may be included in the distribution engine 736 to cooperate with the array generator 738 in determining a geometry and size for the exemplary array 202 and to determine a degree of redundancy of repeated target areas, repeated sub-arrays, and repeated arrangement motifs of the targets and sub-arrays within an exemplary array 202. The degree of redundancy may be based on the degree of reliability desired or the sensitivity and dependability of certain clones or certain test procedures. A redundancy engine 742 may also impart a higher degree of reliability and coverage to an exemplary array 202 by replicating the entire exemplary array 202 a certain number of times, for example, on a single substrate. The amount of redundancy to be imparted can be related to the perceived diagnostic efficacy of the array 202 or part of the array 202. The exemplary array engine 200 described above is one way of producing an exemplary diagnostic array 202.

Exemplary Diagnostics Engine 206

Figure 8:
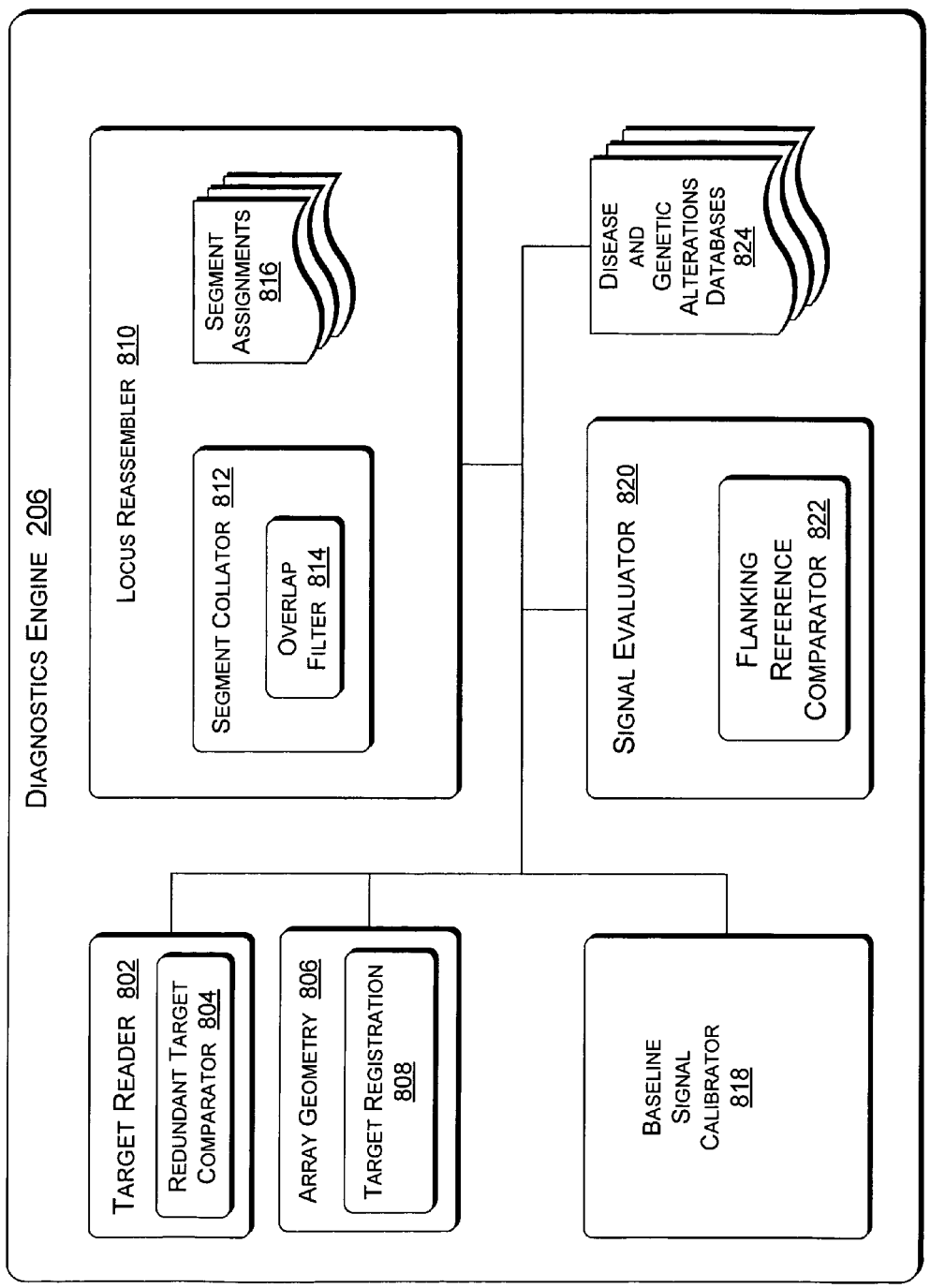
FIG. 8 is a block diagram of an exemplary diagnostics engine.

FIG. 8 shows an exemplary diagnostics engine 206 that exploits the features of an exemplary array 202 produced by an exemplary array engine 200 to yield genetic diagnoses that are more convenient, less expensive, more accurate, and more reliable than conventional diagnoses.

As with the exemplary array engine 200 described above, the various components of an exemplary diagnostics engine 206 are logic modules or, may be combinations of software, firmware, and/or hardware, and may include components or processes that can be performed manually in some implementations. In other words, the components of an exemplary diagnostics engine 206 represent modules of logic or processes that can be included in achieving precision genetic diagnoses using an exemplary array 202.

A target reader 802 is typically included in a diagnostics engine 206 and of course may be a conventional part of a system that processes the kind of test selected for the exemplary array 202, for example, if the exemplary array 202 is a CGH microarray, then the target reader 802 can be a conventional part of a CGH microarray analyzer.

A redundant target comparator 804 may be included in conjunction with the target reader 802 to determine a test result for one type of clone by comparing test results from multiple copies of the clone located in redundant targets across the exemplary array 202.

Array geometry 806 and target registration 808 may be included in the diagnostics engine 206. That is, the strategic placement of targets is stored in a memory or otherwise recorded and used to locate targets, especially redundantly replicated targets that have been isolated from each other. Alternatively, in some implementations the array geometry and placement of targets within the logical structure of the exemplary array 202 may be calculated according to a stored or built-in schema.

A locus reassembler 810 is communicatively coupled with the diagnostics engine 206 to collate individual test results from the clones representing the segments of a locus. By collating test results from individual targets, the locus reassembler 810 obtains an overall combined test result for the base-pair sequence of the entire locus. Thus, a locus reassembler 810 may include a segment collator 812 and an overlap filter 814 to combine test results from individual targets to obtain or calculate a logical test result, such as a representative signal, for the locus that the segments represent. If the correlation between a given target and its associated segment is not derivable by a schema, e.g., if there is no underlying order that can be derived by target registration 808, then the segment collator 812 may consult a database of segment assignments 816 (e.g., as generated by the array engine 200) to relate each target to a segment or to a control reference, etc.

A baseline signal calibrator 818 may determine a signal threshold against which positive and negative test results may be determined. The baseline signal calibrator 818 may take an average of at least some of the test results to calibrate an average signal strength. For example, in CGH, the strength of a fluorescence signal may be influenced by many factors, including the stringency of the test conditions, the quality of the equipment used to analyze results, etc. Additionally, the baseline signal calibrator 818 may examine the signal strength of flanking control references to determine the specific relative characteristics of a typical positive or negative signal result for the test at hand.

A signal evaluator 820 receives a logically collated test result for each locus and may compare the test result with the baseline signal obtained from the baseline signal calibrator 818. A flanking reference comparator 822 may also be included to compare the test result for a given locus with flanking control reference(s) added for comparison to an array 202. In modalities such as CGH, an evaluation that the test result for a given locus is unremarkable or "normal" as opposed to an evaluation that the test result implies genetic alteration can usually be made either from the absolute strength of the signal, from a comparison with the baseline signal, and/or from a comparison with the flanking reference.

A genetic alterations database 824 may also be included to link an evaluation (that is, an evaluation that a particular locus possesses genetic alteration) with a known genetic disease or condition.

Exemplary Methods

Figure 9:
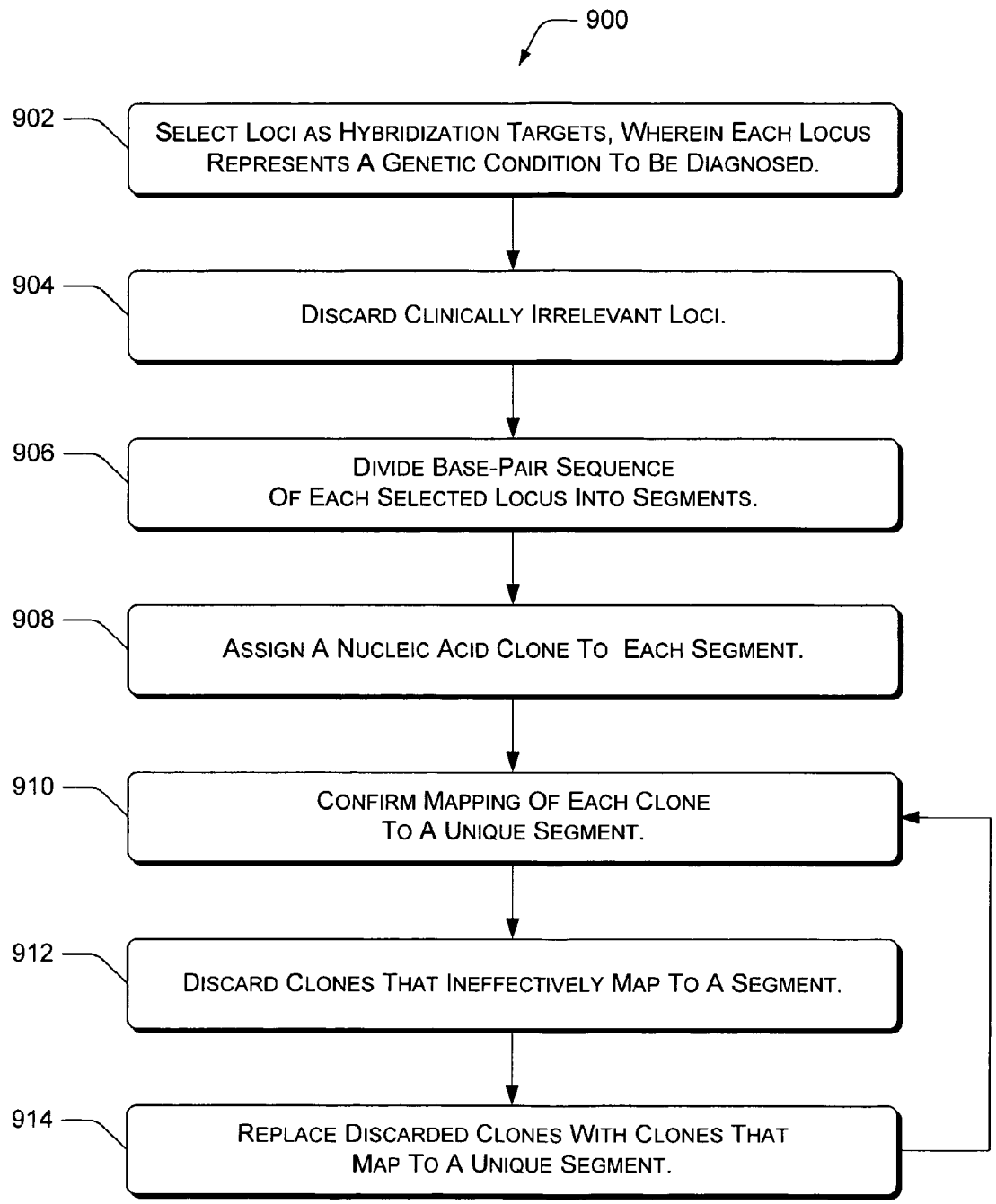
FIG. 9 is a flow diagram of an exemplary method of selecting chromosomal loci.

FIG. 9 shows an exemplary method 900 of selecting chromosomal loci. In the flow diagram, the operations are summarized in individual blocks. The method 900 may be performed by hardware, software, or combinations of both, for example, by an exemplary selection engine 700 and other components of an exemplary array engine 200.

At block 902, chromosomal loci are selected that are capable of representing a genetic alteration or genetic condition to be diagnosed. The selection aims to choose only loci with reliable diagnostic significance—that is, not only chromosomal loci at which genetic alteration is indicative of disease but also loci that are reliably readable for making a diagnosis. In some implementations, selection is automated by selecting from a set of diagnostic loci databases 704 from which a clinical relevance evaluator 706 decides which loci are to be included in an exemplary set. Selection can also be manual, resulting in handpicked loci that represent a set of diseases and that demonstrate diagnostic reliability.

At block 904, clinically irrelevant loci are discarded. A "whole genome" approach is abandoned as too imprecise for a clinical setting, costly in follow up of clinically irrelevant loci; and individual loci selected above at block 902 are eliminated from an exemplary array 202 if they do not test for a disease or yield other clinically relevant information.

At block 906, the base-pair sequence of each selected chromosomal locus is divided into segments. This may be accomplished by a segment assignment engine 714 that implements segmentation. This sequence-division logic may divide a base-pair sequence into segments, e.g., randomly; based on segment length; based on reactivity of the segments; or again based on other factors, such as availability of nucleic acid clones to represent the segments, etc. An overlap engine 716 may implement logic to obtain segments whose adjacent ends cover the same base-pairs of the sequence.

At block 908, a nucleic acid clone (or alternatively a synthetic oligonucleotide) is assigned to each segment. The assignment may be accomplished by logic that links the base-pair sequence of a segment to an available clone from a clone library 720. Alternatively, a clone synthesizer 722 may custom-produce an oligonucleotide to represent the base-pair sequence of a segment. In one implementation, a large insert clone, such as a bacterial artificial chromosome (BAC), a yeast artificial chromosome (YAC), a P1-derived artificial chromosome (PAC), a cosmid, a plasmid, or a cDNA is selected to represent the base-pair sequence of a segment.

At block 910, the mapping of each clone or oligonucleotide to its respective segment of the chromosomal locus is confirmed, for example, by a FISH verifier 708. Confirmation includes verifying that a given clone uniquely maps to one segment and not to multiple segments, loci, or chromosomes. Confirmation may also include verifying the reliability of the mapping under various test conditions of variable stringency.

At block 912, clones that ineffectively map to a segment are discarded. A clone that demands, for proper mapping, test conditions that are too stringent or that are unique may fail the confirmation step as well as clones that do not map to the correct chromosomal locus, clones that hybridized to multiple loci in the genome, clones that cross-hybridized to another chromosome, and clones that hybridized poorly under constant FISH conditions.

At block 914, clones that were discarded at block 912 are replaced by different clones that map properly to respective chromosomal loci and that can demonstrate proper mapping within the stringency tolerances of likely test conditions. The logic of a clone assignor 718 may cooperate with the logic of a segment assignment engine 714 in a "stair step" approach wherein either the segment assignment engine 714 first suggests a proposed segment or alternatively, the clone assignor 718 first suggests a proposed known clone. A dialogue between the two logic modules may ensue in which either can accept a proposal of the other or reject a proposal of the other and suggest an alternative. Proceeding back and forth in proposal-rejection-counterproposal dialogue, the two modules arrive at an acceptable set of segments to represent a chromosomal locus and a set of actual clones to represent the segments.

Figure 10:
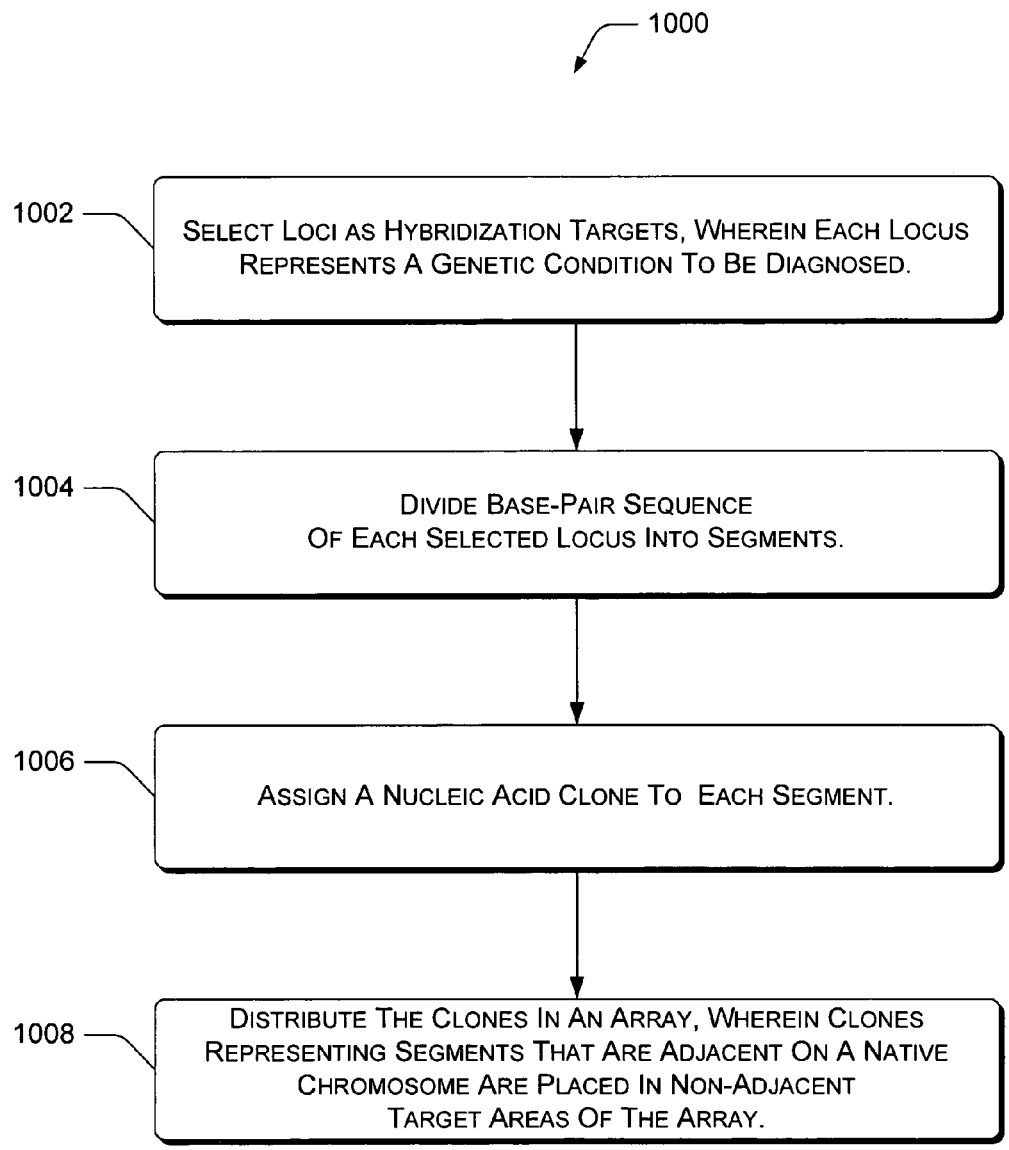
FIG. 10 is a flow diagram of an exemplary method of distributing clones in an exemplary array.

FIG. 10 shows an exemplary method 1000 of distributing clones on an exemplary array. In the flow diagram, the operations are summarized in individual blocks. The method 1000 may be performed by hardware, software, or combinations of both, for example, by an exemplary distribution engine 736 and other components of an exemplary array engine 200.

At block 1002, chromosomal loci are selected that are capable of representing a genetic alteration or genetic condition to be diagnosed. The selection aims, as at block 902, to choose only loci with reliable diagnostic efficacy—that is, not only chromosomal loci that are capable of genetic alteration indicative of disease but also loci that are reliably readable for making a diagnosis.

At block 1004, the base-pair sequence of each selected chromosomal locus is divided into segments, as above at block 906.

At block 1006, a nucleic acid clone or a synthetic oligonucleotide is assigned to each segment, as above at block 908.

At block 1008, the assigned clones (or oligonucleotides) are distributed on an exemplary array 202, for example, according to logic of a distribution engine 736. On an exemplary array 202, for a clone to avoid hybridization effects caused by an adjacent clone that represents a segment that is adjacent on a native chromosome, the clones are separated, that is, placed in non-adjacent targets of an exemplary array 202. Thus, for example, when the exemplary array 202 is exposed to test DNA and control DNA for CGH, inaccuracy and unreliability are not introduced for a given array target by interference from hybridization reactions that would occur if adjacent clones represented adjacent sequences on the native DNA.

Figure 11:
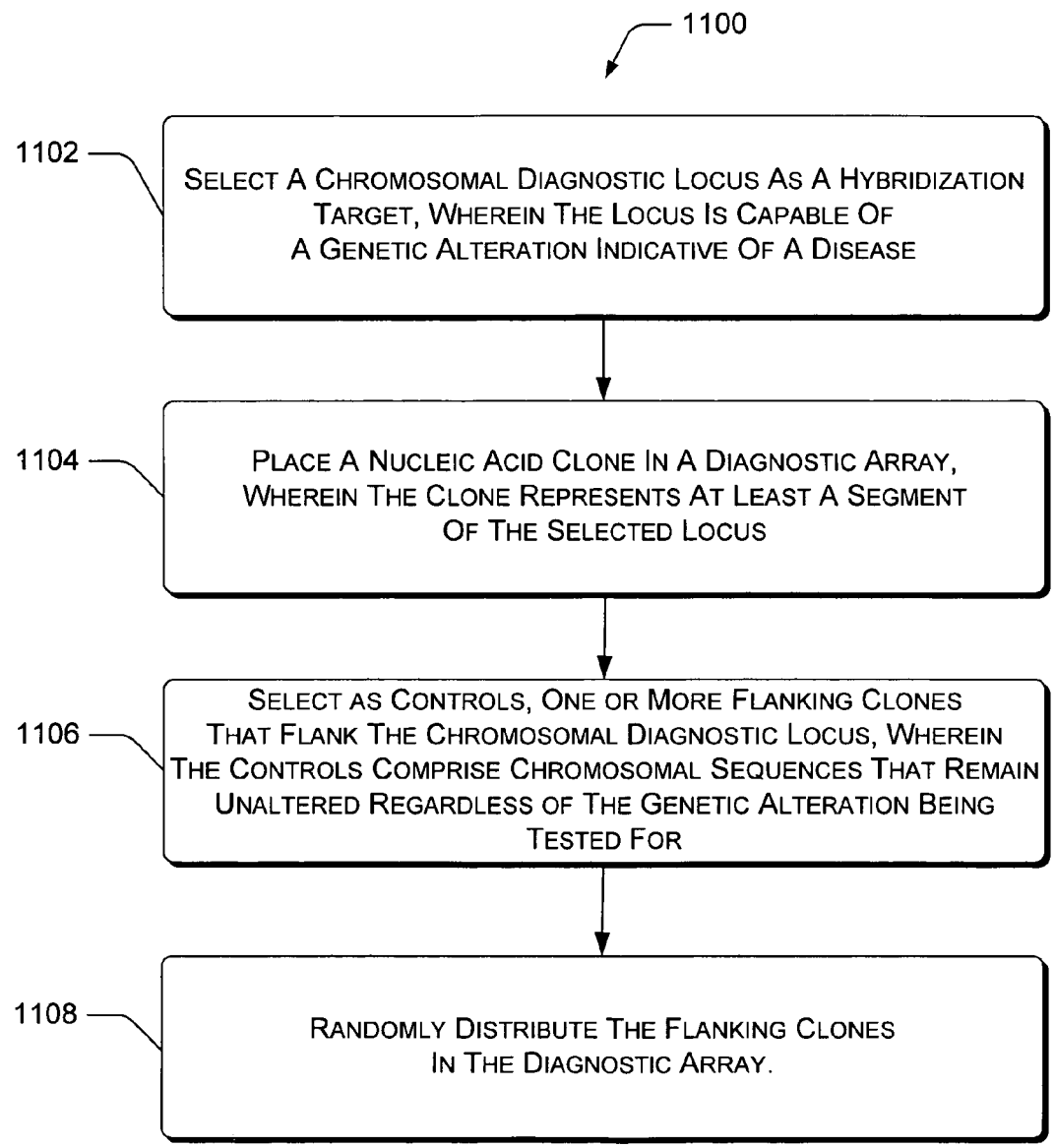
FIG. 11 is a flow diagram of an exemplary method of adding flanking controls to clinically relevant chromosomal loci on an array.

FIG. 11 shows an exemplary method 1100 of flanking clinically relevant chromosomal loci with controls on an array. In the flow diagram, the operations are summarized in individual blocks. The method 1100 may be performed by hardware, software, or combinations of both, for example, by an exemplary reference engine 724 and other components of an exemplary array engine 200.

At block 1102, a chromosomal diagnostic locus is selected as a hybridization target. The locus is capable of genetic alteration indicative of a clinically relevant disease or condition.

At block 1104, a nucleic acid clone is placed on an array, such as an exemplary array 202, wherein the clone represents at least a segment of the selected locus. The clone may be placed more than once on an array, for example according to logic of a redundancy engine 742.

At block 1106, one or more flanking clones are selected as controls. The controls comprise chromosomal sequences that remain unaltered regardless of the genetic alteration being tested for at the chromosomal diagnostic locus. That is, the control typically comprises a clone of chromosomal material that maintains a constant base-pair sequence and dosage in individuals who carry the genetic alteration being tested for at the chromosomal locus selected at block 1102. Such a flanking control provides a reference for comparing an array target against a control sequence that was adjacent to the target on the chromosome. For example, in CGH, the reference target provides an intensity of a fluorescence signal that should be present and unaltered in individuals who manifest the genetic alteration at the chromosomal diagnostic locus of interest, and this reference signal is helpful because it is from a clone that represents a sequence adjacent to the target on the native chromosome.

At block 1108, the flanking clones are randomly distributed across an exemplary array 202. Thus, without being affected by proximity to a chromosomal diagnostic locus on an array 202, clones of sequences that flank the diagnostic locus on the chromosome can be tested apart from the chromosomal locus for purposes of comparison and reference.

Figure 12:
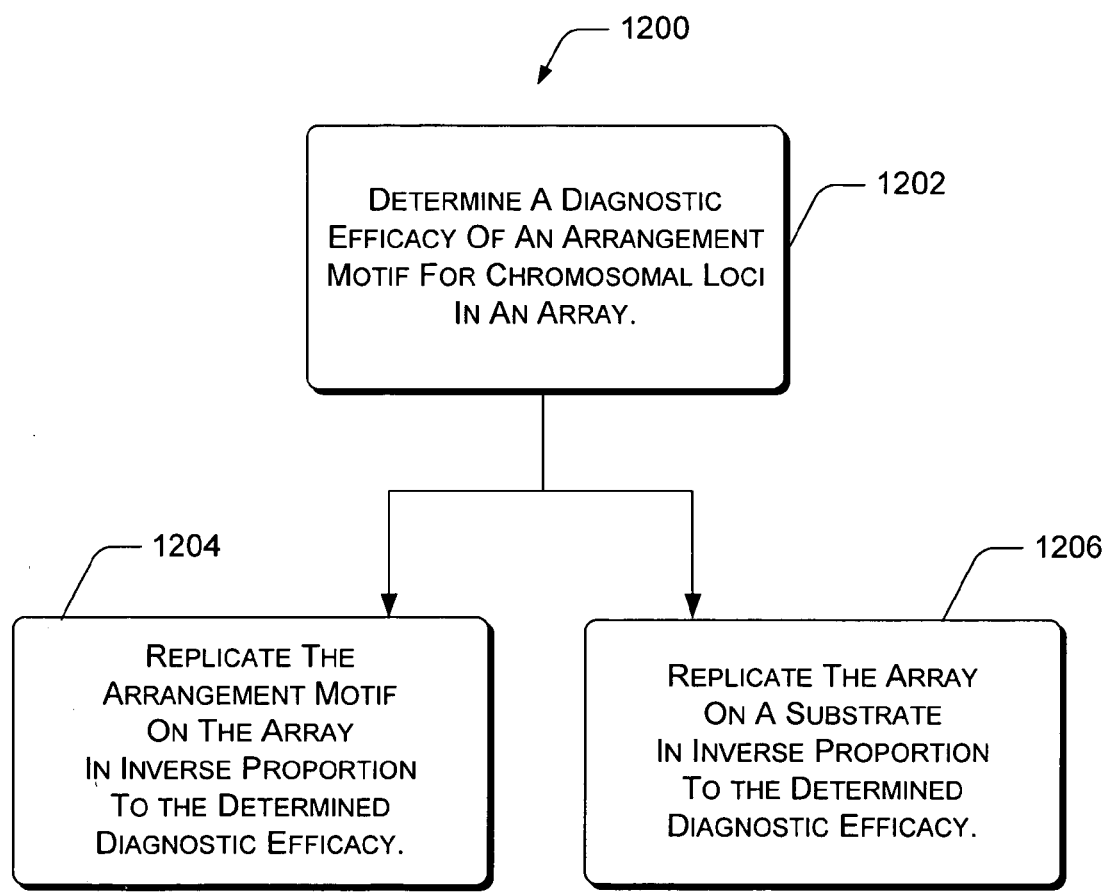
FIG. 12 is a flow diagram of an exemplary method of replicating an arrangement motif for chromosomal loci on an array in inverse proportion to a determined diagnostic efficacy of the motif.

FIG. 12 shows an exemplary method 1200 of replicating an arrangement motif for chromosomal loci on an array. In the flow diagram, the operations are summarized in individual blocks. The method 1200 may be performed by hardware, software, or combinations of both, for example, by an exemplary redundancy engine 742 and other components of an exemplary array engine 200.

At block 1202, a diagnostic efficacy of an arrangement motif for chromosomal loci in an array is determined. The arrangement motif may be simple, such as the motif of a single array target adjacently flanked by a single reference target, or may be more complex such as the layout of an entire sub-array of an exemplary array 202, wherein targets that represent adjacent segments of a native chromosome are placed non-contiguously on the exemplary array 202. Then too, an exemplary motif may be the arrangement of only those clones that represent segments of a single chromosomal locus. Yet again, an exemplary arrangement motif may be multiple small-scale arrangement motifs within a larger-scale arrangement motif, for example, an exemplary array 202 containing multiple repeating sub-arrays that is itself capable of being redundantly repeated on an even larger substrate. The diagnostic efficacy of one or more of these arrangement motifs may be determined theoretically or actually. The more reliable the motif for yielding diagnostic results, the fewer times the motif may need to be redundantly repeated via this exemplary method 1200.

Thus, at block 1204 the arrangement motif is replicated on an exemplary array 202 multiple times. An arrangement motif that is useful but not very dependable or that is not very forgiving of less than stringent test conditions may be replicated many times on an exemplary array 202. Conversely, a very dependable motif may be replicated only a few times or included only in its original form in order to conserve resources.

In one implementation, replicating an arrangement motif may include creating an orientation marking or design for positioning an array 202 during testing. The orientation marking(s) or design may be implemented by arranging the targets themselves, for example, by creating a non-symmetric arrangement of the targets on the array 202 to form an arrow, or other directional indicator. The directional indicator(s) allow correct orientation of the array 202, e.g., during insertion of the array 202 into a diagnostics engine 206. These orientation markings or design let a machine and/or human operator recognize an array's orientation.

At block 1206, an array implementation that includes ample targets to test for each genetic alteration once may itself be replicated a number of times in inverse proportion to the determined or hypothesized diagnostic efficacy of the array as a whole or a part of the array—even a single target. In one implementation, the amount of redundancy imparted to an exemplary array 202 derives from the least dependable element of the array.

Exemplary Implementation

In one implementation, the diagnostic loci databases 704 of the array engine 200 included genome resources, such as the Marshfield Genetic Map Marshfield Clinic at Marshfield Center, Marshfield, Wis. USA). Selection engine logic 700 chose clinically relevant chromosomal loci for potential clone assignment from loci known to be involved in dosage imbalances that result in clinically relevant diseases, including known microdeletion syndromes, known microduplication syndromes, and terminal deletion syndromes, as shown in Table 1:

TABLE 1

CLINICALLY RELEVANT MICORODELETION AND MICRODUPLICATION LOCI

| Disorder | Locus | Location |
| --- | --- | --- |
| MONOSOMY 1P | MULTIPLE | 1P36 |
| HOLOPROSENCEPHALY 2 | SIX3 | 2P21 |
| NEPHRONOPHTHISIS | NPHP1 | 2Q13 |
| HOLOPROSENCEPHALY 6 | MULTIPLE | 2Q37 1-27.3 |
| WOLF-HIRSCHHORN | MULTIPLE | 4P16 |
| CRI-DU-CHAT | MULTIPLE | 5P15 |
| CORNELIA DE LANGE | NIPBL | 5P13 |
| SAETHRE-CHOTZEN | TWIST | 7P21 |
| GREIG CEPHALOPOLYSYNDACTYLY | GL13 | 7P13 |
| WILLIAMS SYNDROME | ELN | 7Q11.23 |
| HOLOPROSENCEPHALY 3 | SHH | 7Q36 |
| CHARGE SYNDROME | CHD7 | 8Q12.1 |
| LANGER-GIEDION | EXT1 | 8Q24 |
| TRICHORHINOPHALANGEAL SYNDROME | TRPS1 | 8Q24 |
| HOLOPROSENCEPHALY 7 | PATCH | 9Q22.3 |
| DIGEORGE SYNDROME II | MULTIPLE | 10P13 |
| BECKWITH-WIEDEMANN | IGF2 | 11P15.5 |
| WAGR SYNDROME | WNT, PAX6 | 11P13 |
| POTOCKI-SHAFFER SYNDROME | EXT2, ALX4 | 11P11.2 |
| NOONAN SYNDROME | PRPN11 | 12Q24.1 |
| RETINOBLASTOMA/MR | RB1 | 13Q14 |
| HOLOPROSENCEPHALY 5 | ZIC2 | 13Q32 |
| PRADER-WILLI SYNDROME | SNRPN | 15Q12 |
| ANGELMAN SYNDROME | UBE3A | 15Q12 |
| RUBINSTEIN-TAYBI | CREBBP | 16P13.3 |
| TUBEROUS SCLEROSIS | TSC2 | 16P13.3 |
| POLYCYSTIC KIDNEY DISEASE | PKD1 | 16P13.3 |
| MILLER-DIEKER SYNDROME | LIS1 | 17P13.3 |
| CHARCOT-MARIE-TOOTH DISEASE | PMP22 | 17P12 |
| SMITH-MAGENIS SYNDROME | RAI1 | 17P11.2 |
| DUPLICATION PROXIMAL 17 | MULTIPLE | 17P11.2 |
| NEUROFIBROMATOSIS I | NF1 | 17Q11.2 |
| HOLOPROSENCEPHALY 4 | TGIF | 18P11.3 |
| ALAGILLE SYNDROME | JAG1 | 20P11.23 |
| HOLOPROSENCEPHALY 1 | TMEM1/ EHOC1 | 21Q22.3 |
| DIGEORGE SYNDROME I | TUPLE1/TBX1 | 22Q11.2 |
| STEROID SULFATASE DEFICIENCY | STS | XP22.3 |
| MICROPHTHALMIA WITH LINEAR SKIN DEFECTS | MULTIPLE | XP22.3 |
| GLYCEROL KINASE DEFICIENCY | GK | XP21 |
| ADRENAL HYPOPLASIA CONGENITA | DAX1 | XP21 |
| DUCHENNE MUSCULAR DYSTROPHY | DYSTROPHIN | XP21 |
| PELIZAEUS-MERZBACHER DISEASE | PLP1 | XQ21 |
| X-LINKED HETEROTAXY | ZIC3 | XQ26.2 |
| SEX DETERMINING FACTOR | SRY | YP11.3 |

Pericentromeric and telomeric loci were also selected. These loci were uniquely selected to identify aneuploidy (extra or missing chromosomes), deletions or duplications of the telomeric regions, deletions or duplications of the pericentromeric regions, marker chromosomes, and unbalanced derivative chromosomes, as shown below in TABLE 2:

TABLE 2

PERICENTROMERIC AND TELOMERIC LOCI
Chromosome Region

1P36.3
1P12
1Q21
1Q44
2P25.3
2P11.2

TABLE 2-continued

PERICENTROMERIC AND TELOMERIC LOCI
Chromosome Region

2Q11.2
2Q37.3
3P26.3
3P11.2
3Q11.2
3Q29
4P16.3
4P12
4Q12
4Q35.2
5P15.3
5P12
5Q11.2
5Q35.3
6P25.3
6P11.2
6Q12
6Q27
7P22.3
7P11.2
7Q11.21
7Q36.3
8P23.3
8P11.2
8Q11.2
8Q24.3
9P24.3
9P11.2
9Q13
9Q34.3
10P15.3
10P11.21
10Q11.21
10Q26.3
11P15.5
11P11.2
11Q12
11Q25
12P13.33
12P11.21
12Q12
12Q24.33
13Q12.11
13Q34
14Q11.2
14Q32.33
15Q11.2
15Q26.3
16P13.3
16P11.2
16Q21.1
16Q24.3
17P13.3
17P11.2
17Q11.2
17Q
18P11.32
18P11.21
18Q11.2
18Q23
19P13.3
19P12
19Q12
19Q13.43
20P13
20P11.21
20Q11.21
20Q13.33
21Q11.2
21Q22.3
22Q11.2
22Q13.3
XP22.3
XP11.22
XQ11.2
XQ28
YP22.3

TABLE 2-continued

PERICENTROMERIC AND TELOMERIC LOCI
Chromosome Region

YP11.3
YP11.2
YQ11.2

For this implementation, locus selection was influenced by availability of clones in the clone libraries 720. A group of approximately nine-hundred BAC clones were considered for representation of the clinically relevant chromosomal loci. A FISH verifier 708 revealed that approximately 7% of the clones were mismapped based on map locations obtained from two publicly available databases (some mapped to the wrong chromosome and some mapped to a different locus on the same chromosome), approximately 17% cross-hybridized to other chromosomes, and approximately 10% either did not hybridize or showed poor hybridization signals under uniform FISH conditions). Thus, only about 65% of clones met selection criteria as applied, for example, by the FISH verifier 708. These selected clones were placed into an exemplary array 202.

The clone assignor 718 identified large-insert clones, mostly BACs, to represent the selected loci, searching by gene, STS marker, or by previous publication of a clone in a clone library 720 to anchor each chromosomal locus of interest.

The segment assignment engine 714 developed a contiguous segment strategy to cover each locus of interest. A minimum of three overlapping clones was selected to cover segments of each locus to be represented on the exemplary array 202. A FISH verifier 708, employing uniform experimental conditions on a single control male whose genetic material was used throughout this trial, confirmed that each clone mapped properly to its respective chromosomal locus. The FISH verifier 708 rejected clones that did not map to the correct chromosomal locus, clones that hybridized to multiple loci in the genome, clones that cross-hybridized to another chromosome, and clones that hybridized poorly under these constant FISH conditions.

Segment assignment engine 714 replaced the rejected clones with BACs that properly map to respective chromosomal loci as suggested by the diagnostic loci databases 704 and as confirmed by the FISH verifier 708.

At known microdeletion and microduplication loci in which structural rearrangements are mediated by low copy repeat (LCR) regions that flank the deleted or duplicated locus, a telomeric sequence selector 728 and a centromeric sequence selector 730 of the reference engine 724 selected "control" BAC contigs outside the LCR regions, adjacent on either side of the locus. No BACs that map to the LCRs were selected.

Array design logic in accordance with the array generator 738, the target isolation engine 740, and the redundancy engine 742 of the distribution engine 736 was implemented to construct the exemplary array 202. To ensure that no particular area of the exemplary array 202 would cause deletion misclassifications because of naturally contiguous clones adjacent to each other on the exemplary array 202, distribution logic of the target isolation engine 740 placed each clone selectively in a 384-well plate (c.f., FIG. 5). The redundancy engine 742 called for printing the plate four times on the exemplary array 202.

Implementation details include insert-DNA extraction with a RPM SPIN MIDI KIT followed by sonicating 5 μg of probe DNA to a final size between 500 bp-20 kb (Q-BIOgene, Carlsbad, Calif., USA). The DNA was precipitated with NaAc 3M pH 5.2 (1:8 of the total volume) and isopropanol (1:1 volume). The DNA was hydrated with sterile water to a final concentration of 625 ng/µl. Before printing the exemplary array 202, 50% DMSO was added with nitrocellulose as has been previously described.

Array printing was conducted with an OMNIGRID ACCENT MACHINE (GeneMachine, San Carlos, Calif., USA) at 30% humidity and a temperature of 24° C. using low-autofluorescence slides (VWR International, West Chester, Pa., USA) treated with aminosilane (Sigma-Aldrich, Sheboygan Falls, Wis., USA). Printed slides were baked at 80° C. from 4 hours to overnight and then washed with 80° C. millipore water for 2 minutes and cold ethanol of 95% for 1 minute. Blocking of the slides was achieved with 10% bovine serum albumin fraction V (Sigma, St. Louis, Mo., USA) and 20 µg salmon sperm DNA (Invitrogen, Carlsbad, Calif., USA) in a humid chamber at 45° for 2 hours. Slides were denatured in boiling millipore water, then dehydrated with 95% ethanol at −20° C. and stored in a desiccator.

Genomic DNA was extracted with a PUREGENE DNA ISOLATION KIT from lymphoblastoid cell lines, peripheral blood, or cultured tissues of the subjects and phenotypically normal male and female references (Gentra Systems, Inc. Minneapolis, Minn., USA). Genomic DNA was digested with Dpn II (New England Biolabs, Inc., Beverly, Mass., USA) and reprecipitated (1:8 volume of NaAc 3M pH5.2 and 1:1 volume of isopropanol).

In one implementation, a dye-reversal strategy was used on two separate exemplary arrays 202 in which 500 ng of both subject and reference DNAs were labeled (BIO PRIME DNA LABELING SYSTEM, Invitrogen) with CY3 dye and CY5 dye, respectively.

The subject and reference DNA were co-hybridized to a first exemplary array 202 and then oppositely labeled and co-hybridized to a second exemplary array 202. Shortly after the labeling, probes were purified with MICROCON filter units (Millipore, Billerica, Mass., USA), and ~500 ng of subjects' DNA, combined with an equal amount of reverse-sex control DNA, was co-precipitated with 50 µg of Cot1-DNA (Invitrogen) and hydrated with 15.5 µl ULTRAHYB (Ambion, Austin, Tex., USA). The labeled genomic DNAs were denatured at 72° C. for 5 minutes, preannealed immediately after at 37° C. for 1 hour, placed onto an exemplary array 202, and covered with a 22×22 mm coverslip.

For the test 204, hybridization was performed in an incubation chamber (Corning Incorporated Life Sciences, Acton, Mass., USA) at 37° C. with shaking for 14-16 hours. Following the hybridization, the coverslips were removed with 1×PBS and the exemplary arrays 202 were washed with 50% formamide+2×SSC+0.1% SDS at 45° C. for 20 minutes and 1×PBS for 20 minutes at room temperature in the dark. The exemplary arrays 202 were then rinsed with 0.2×SSC and millipore water and dried immediately.

A target reader 802 comprising in part a GENEPIX 4000B dual-laser scanner and individual spots were analyzed with GENEPIX PRO 4.0 imaging software (Axon Instruments, Union City, Calif., USA). Two simultaneous scans of each array were obtained at wavelengths of 635 nm and 532 nm. The average ratios of four spots for each subject were analyzed with ACUITY 3.0 software (Axon Instruments, Union City, Calif., USA). Thresholds for copy-number gain and loss were set at 1.5 and 0.5, respectively. After subtraction of background noise, the ratio of fluorescence intensities derived from hybridized test and control DNA was calculated and normalized by the ratios measured from reference targets on the same slide. These reference targets always contained DNA that was of the same complexity as the target spots of the selected chromosomal loci of interest.

Results were verified using FISH. More specifically, DNA was extracted from BAC clones using a standard alkaline lysis protocol and labeled by nick translation with biotin-dUTP or digoxigenin-dUTP (Roche Diagnostic, Indianapolis, Ind., USA). The probes were denatured at 70° C. for 10 minutes and hybridized to denatured metaphase chromosomes on microscope slides at 37° C. The following day the slides were washed with 50% formamide at 42° C. for 15 minutes, 2×SSC at 37° C. for 8 minutes, and 1×PBD at room temperature for 2 minutes. The signals were amplified with FITC-avidin (Sigma) and anti-avidin (Sigma) to detect the biotin-dUTP, and with anti-digoxigenin monoclonal antibody, anti-mouse IgG-digoxigenin and anti-digoxigenin-rhodamine FAB fragments (Sigma) to detect the dig-dUTP. The slides were counterstained with DAPI. Cells were examined with a ZEISS AXIOPLAN II fluorescence microscope equipped with a triple-bandpass filter that allows multiple colors to be visualized simultaneously. Digital images were captured and stored with ISIS software V 3.4.0 (Metasystems, Altlussheim, Germany).

Exemplary Results

The exemplary array 202 identified deletion and duplication polymorphisms in the phenotypically normal individuals and detected all of the expected chromosomal alterations in the patients with known abnormalities. In addition, previously undetected clinically relevant abnormalities were revealed by the exemplary array 202. The abnormalities detected by the exemplary array 202 were confirmed via FISH as described above.

A previously undetected terminal deletion of 14q was identified by the exemplary array 202 in an individual who was studied previously with telomere FISH analysis. This deletion was subsequently confirmed by FISH. In general, the exemplary array 202 allowed accurate and reliable detection of deletions (1:2/dosage difference) and duplications (2:3 dosage difference).

In one implementation, an exemplary array 202 identified a small duplicated segment of 1p36 (~750 kb) that could not be detected using conventional mapping techniques. The exemplary array 202 proved invaluable for detecting this cryptic complex rearrangement.

An exemplary array 202 was also useful in detecting gene dosage differences and in the detection of female carriers of deletions on the X chromosome. The exemplary array 202 was particularly useful in identifying female carriers of Duchenne muscular dystrophy (DMD) deletions.

CONCLUSION

The subject matter described above can be implemented as logic modules, methods, clinical processes, diagnostic array articles, hardware, software, and various combinations of each of these. In certain implementations, the subject matter may be described at least in part in the general context of computer-executable instructions, such as program modules, being executed by a computing device or communications device. Generally, program modules include routines, programs, objects, components, data structures, etc. that perform particular tasks or implement particular abstract data types.

The foregoing discussion describes exemplary methods and apparatuses for achieving precision genetic diagnoses. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method, comprising:
    selecting a set of genetic diseases associated with a set of corresponding chromosomal loci, each chromosomal locus associated with at least one genetic disease of the genetic diseases, and each genetic disease in the set of genetic diseases associated with a genetic alteration of a corresponding chromosomal locus of the set of chromosomal loci;
    selecting nucleic acid molecules to represent each chromosomal locus;
    arranging segments of the nucleic acid molecules on a microarray to represent the chromosomal loci associated with the set of genetic diseases; and
    isolating the segments associated with the same chromosomal locus in non-adjacent target areas of the microarray; and
    wherein the set of corresponding chromosomal loci comprises: 1p36.3, 1p12, 1q21, 1q44, 2p25.3, 2p11.2, 2q11.2, 2q37.3, 3p26.3, 3p11.2, 3q11.2, 3q29, 4p16.3, 4p12, 4q12, 4q35.2, 5p15.3, 5p12, 5q11.2, 5q35.3, 6p25.3, 6p11.2, 6q12, 6q27, 7p22.3, 7p11.2, 7q11.21, 7q36.3, 8p23.3, 8p11.2, 8q11.2, 8q24.3, 9p24.3, 9p11.2, 9q13, 9q34.3, 10p15.3, 10p11.21, 10q11.21, 10q26.3, 11p15.5, 11p11.2, 11q12, 11q25, 12p13.33, 12p11.21, 12q12, 12q24.33, 13q12.11, 13q34, 14q11.2, 14q32.33, 15q11.2, 15q26.3, 16p13.3, 16p11.2, 16q21.1, 16q24.3, 17p13.3, 17p11.2, 17q11.2, 17q, 18p11.32, 18p11.21, 18q11.2, 18q23, 19p13.3, 19p12, 19q12, 19q13.43, 20p13, 20p11.21, 20q11.21, 20q13.33, 21q11.2, 21q22.3, 22q11.2, 22q13.3, Xp22.3, Xp11.22, Xq11.2, Xq28, Yp22.3, YP11.3, Yp11.2, and YQ11.2.

2. The method as recited in claim 1, further comprising:
    hybridizing a nucleic acid sample from an individual human to the microarray; and
    detecting a genetic alteration via one of the segments on the microarray to diagnose one of the genetic diseases.

3. The method as recited in claim 2, further comprising:
    when hybridization fails in one of the target areas of the microarray, detecting the genetic alteration associated with the genetic disease via a segment of the nucleic acid molecule representing the chromosomal locus associated with the genetic disease in a different target area of the microarray.

4. The method as recited in claim 1, further comprising:
    for each chromosomal locus associated with the set of genetic diseases, randomly placing a first segment associated with the chromosomal locus at a random location on the microarray; and
    for the first segment and the remaining segments associated with each chromosomal locus, maximizing an isolation distance of the segments from each other on the microarray.

5. The method as recited in claim 1, further comprising synthesizing flanking oligomers to represent a chromosomal region flanking a chromosomal locus; and
    including the flanking oligomers on the microarray to test for an extent of the genetic alteration associated with the chromosomal locus.

6. The method as recited in claim 1, wherein the chromosomal loci are capable of indicating deletion and duplication syndromes, including Holoprosencephaly 2, Nephronophthisis, Holoprosencephaly 6, Wolf-Hirschhorn, Cri-du-Chat, Saethre-Chotzen, Greig cephalopolysyndactyly, Williams syndrome, Holoprosencephaly 3, Langer-Giedion, Trichorhinophalangeal syndrome, Holoprosencephaly 7, DiGeorge syndrome II, Beckwith-Wiedemann, WAGR syndrome, Potocki-Shaffer syndrome, Noonan syndrome, Retinoblastoma/MR, Holoprosencephaly 5, Prader-Willi syndrome, Angelman syndrome, Rubinstein-Taybi Syndrome, Tuberous sclerosis, Polycystic kidney disease, Miller-Dieker syndrome, Smith-Magenis syndrome, Duplication proximal 17, Neurofibromatosis I, Holoprosencephaly 4, Alagille syndrome, Holoprosencephaly 1, DiGeorge syndrome I, Steroid sulfatase deficiency, Microphthalmia with linear skin defects, Glycerol kinase deficiency, Adrenal hypoplasia congenita, Duchenne muscular dystrophy, Pelizaeus-Merzbacher disease, and alterations of sex determining factor.

7. A method, comprising:
    selecting a set of genetic diseases associated with a set of corresponding chromosomal loci, each genetic disease in the set of genetic diseases associated with a genetic alteration of a corresponding chromosomal locus;
    selecting nucleic acid molecules to represent each chromosomal locus;
    synthesizing segments of the nucleic acid molecules as oligomers;
    placing the oligomers on a microarray to represent the chromosomal loci associated with the set of genetic diseases;
    isolating the oligomers associated with the same chromosomal locus in non-adjacent target areas of the microarray to provide a reliable diagnosis of the genetic alteration when one of the target areas fails; and
    wherein the set of corresponding chromosomal loci comprises: 1p36.3, 1p12, 1q21, 1q44, 2p25.3, 2p11.2, 2q11.2, 2q37.3, 3p26.3, 3p11.2, 3q11.2, 3q29, 4p16.3, 4p12, 4q12, 4q35.2, 5p15.3, 5p12, 5q11.2, 5q35.3, 6p25.3, 6p11.2, 6q12, 6q27, 7p22.3, 7p11.2, 7q11.21, 7q36.3, 8p23.3, 8p11.2, 8q11.2, 8q24.3, 9p24.3, 9p11.2, 9q13, 9q34.3, 10p15.3, 10p11.21, 10q11.21, 10q26.3, 11p15.5, 11p11.2, 11q12, 11q25, 12p13.33, 12p11.21, 12q12, 12q24.33, 13q12.11, 13q34, 14q11.2, 14q32.33, 15q11.2, 15q26.3, 16p13.3, 16p11.2, 16q21.1, 16q24.3, 17p13.3, 17p11.2, 17q11.2, 17q, 18p11.32, 18p11.21, 18q11.2, 18q23, 19p13.3, 19p12, 19q12, 19q13.43, 20p13, 20p11.21, 20q11.21, 20q13.33, 21q11.2, 21q22.3, 22q11.2, 22q13.3, Xp22.3, Xp11.22, Xq11.2, Xq28, Yp22.3, YP11.3, Yp11.2, and YQ11.2.

8. The method as recited in claim 7, wherein said synthesizing segments of the nucleic acid molecules as oligomers further includes synthesizing oligomers that represent overlapping segments of the nucleic acid molecules.

9. The method as recited in claim 7, wherein the chromosomal loci are capable of indicating deletion and duplication syndromes, including Holoprosencephaly 2, Nephronophthisis, Holoprosencephaly 6, Wolf-Hirschhorn, Cri-du-Chat, Saethre-Chotzen, Greig cephalopolysyndactyly, Williams syndrome, Holoprosencephaly 3, Langer-Giedion, Trichorhinophalangeal syndrome, Holoprosencephaly 7, DiGeorge syndrome II, Beckwith-Wiedemann, WAGR syndrome, Potocki-Shaffer syndrome, Noonan syndrome, Retinoblastoma/MR, Holoprosencephaly 5, Prader-Willi syndrome, Angelman syndrome, Rubinstein-Taybi Syndrome, Tuberous sclerosis, Polycystic kidney disease, Miller-Dieker syndrome, Smith-Magenis syndrome, Duplication proximal 17, Neurofibromatosis I, Holoprosencephaly 4, Alagille syndrome, Holoprosencephaly 1, DiGeorge syndrome I, Steroid sulfatase deficiency, Microphthalmia with linear skin defects, Glycerol kinase deficiency, Adrenal hypoplasia congenita, Duchenne muscular dystrophy, Pelizaeus-Merzbacher disease, and alterations of sex determining factor.

* * * * *